(12) United States Patent
Chiu et al.

(10) Patent No.: US 8,827,718 B2
(45) Date of Patent: Sep. 9, 2014

(54) MOTOR COORDINATION TESTING DEVICE

(75) Inventors: Hsiu-Ching Chiu, Kaohsiung (TW); Louise Ada, Sydney (AU); Hsin-Min Lee, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 260 days.

(21) Appl. No.: 13/280,599

(22) Filed: Oct. 25, 2011

(65) Prior Publication Data

US 2013/0101971 A1    Apr. 25, 2013

(51) Int. Cl.
*G09B 19/00* (2006.01)
*A61B 5/107* (2006.01)
*A61B 5/00* (2006.01)
*A61B 5/11* (2006.01)

(52) U.S. Cl.
CPC ............. *A61B 5/1071* (2013.01); *A61B 5/1125* (2013.01); *G09B 19/003* (2013.01); *A61B 5/6824* (2013.01); *A61B 5/4082* (2013.01); *A61B 5/1124* (2013.01); *A61B 2505/09* (2013.01); *A61B 5/6831* (2013.01)
USPC ........................................................ 434/258

(58) Field of Classification Search
USPC .............. 434/258, 260; 602/16; 128/878, 879
See application file for complete search history.

(56) References Cited

U.S. PATENT DOCUMENTS

| | | | | |
|---|---|---|---|---|
| 3,916,537 A | * | 11/1975 | Gilligan et al. | 434/258 |
| 4,738,269 A | * | 4/1988 | Nashner | 600/595 |
| 4,885,687 A | * | 12/1989 | Carey | 434/261 |
| 4,909,262 A | * | 3/1990 | Halpern et al. | 600/587 |
| 5,201,772 A | * | 4/1993 | Maxwell | 623/24 |
| 5,469,862 A | * | 11/1995 | Kovacevic | 600/595 |
| 6,827,579 B2 | * | 12/2004 | Burdea et al. | 434/258 |
| 2009/0062698 A1 | * | 3/2009 | Einav et al. | 601/5 |
| 2009/0131225 A1 | | 5/2009 | Burdea et al. | |

* cited by examiner

*Primary Examiner* — Robert J Utama
*Assistant Examiner* — Sadaruz Zaman
(74) *Attorney, Agent, or Firm* — Alan Kamrath; Kamrath IP Lawfirm, P.A.

(57) ABSTRACT

A motor coordination testing device includes a signal generator and a signal retrieving device. The signal generator includes a first electronic protractor, a second electronic protractor, a first support rotatably coupled with the first electronic protractor, and a second support rotatably coupled with the second electronic protractor. The signal retrieving device is electrically connected to the signal generator.

12 Claims, 8 Drawing Sheets

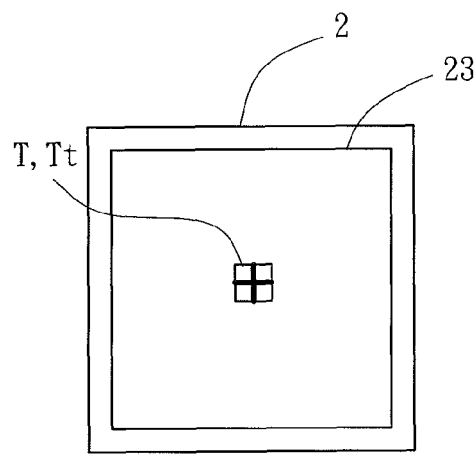
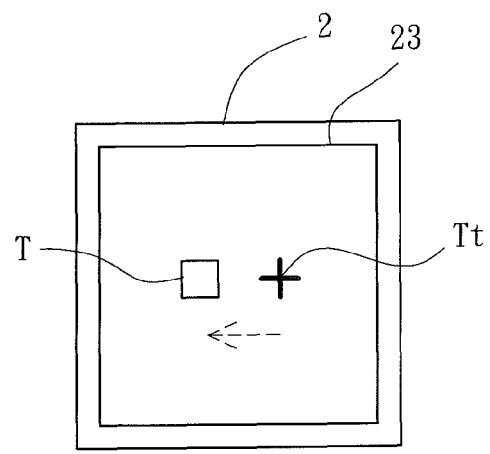
FIG. 6a     FIG. 6b
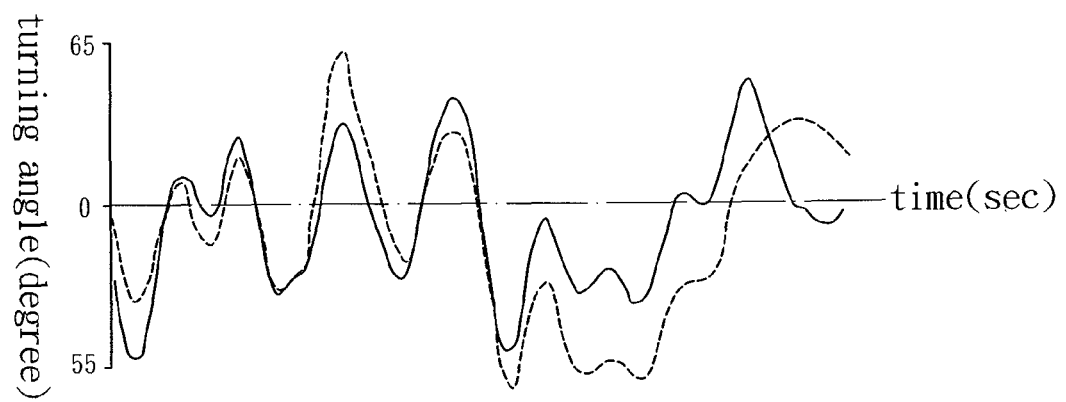
FIG. 7

MOTOR COORDINATION TESTING DEVICE

BACKGROUND OF THE INVENTION

1. Field of the Invention

The present invention generally relates to a motor coordination testing device and a signal generator thereof and, more particularly, to a motor coordination testing device that can test the motor coordination of a testee by providing quantified data, as well as a signal generator thereof.

2. Description of the Related Art

Patients with partial paralysis caused by diseases, such as cerebral palsy or stroke, often have physical disability due to muscle weakness, poor physical coordination, convulsion, contracture, etc. This affects their life badly.

Referring to FIG. 1, a conventional motor coordination testing device including a base 91 and a plurality of cylindrical sticks 92 is shown. The base 91 has a plurality of holes 911 and a recess 912, with the plurality of holes 911 arranged in a matrix form. The cylindrical sticks 92 are disposed in the recess 912 in disorder.

When testing the motor coordination of a testee, the testee is required to pick up the cylindrical sticks 92 one by one, and place each cylindrical stick 92 into a corresponding hole 911 accordingly. Then, the testee is required to pick up the cylindrical sticks 92 again and place them back into the recess 912 to complete the whole procedure. Based on this, the motor coordination of the testee can be determined according to how much time the testee spent on the whole procedure.

However, the above motor coordination testing device tests the motor coordination of the testee only by the amount of time the testee spent on the whole procedure without being able to detect which motions the testee can smoothly perform without any difficulty or which motions the testee has a hard time performing. This problem cannot be overcome unless a person is watching and recording all the motions the testee has performed. Therefore, the conventional motor coordination testing device is incapable of providing any quantified data after the test, making it impossible for a diagnostician to provide a correct analysis using the testing result of the motor coordination testing device.

Furthermore, the conventional motor coordination testing device is not applicable to patients with muscle weakness, because the motor coordination testing device requires the patients to apply muscle strength to pick up the cylindrical sticks 92 and to hold and move the cylindrical sticks 92 with their fingers. In another aspect, since there are many factors that contribute to the testing result, a diagnostician would not be able to know whether the motor disability of the patient is caused by muscle weakness or poor coordination. As a result, the diagnostician may likely give the patient an incorrect recommendation as to rehabilitation.

SUMMARY OF THE INVENTION

It is therefore the primary objective of this invention to provide a motor coordination testing device capable of recording all the information needed by data quantification during the motor coordination test of a testee.

It is another objective of this invention to provide a motor coordination testing device that can test the motor coordination of a testee without requiring the testee to apply much muscle force.

It is yet another objective of this invention to provide a motor coordination testing device that can provide quantified data for further analysis based on electronic signals obtained from turning of a limb of a testee.

The invention discloses a motor coordination testing device including a signal generator and a signal retrieving device. The signal generator includes a first electronic protractor and a first support rotatably coupled with the first electronic protractor. The signal retrieving device is electrically connected to the signal generator.

The signal generator further comprises a second electronic protractor and a second support rotatably coupled with the second electronic protractor. The second electronic protractor is coupled with the first support and electrically connected to the signal retrieving device.

The signal retrieving device comprises a conversion unit, a processing unit and a display unit. The conversion unit is electrically connected to the first electronic protractor and the processing unit, and the processing unit is electrically connected to the display unit.

The second electronic protractor comprises a connection member fixed to the first support, and the first electronic protractor comprises a turning control member controlling whether the first support turns relatively to the first electronic protractor.

The second support comprises a sleeve, a shaft and a finger support. The sleeve is connected to the second electronic protractor, the shaft is extended into the sleeve and protrudes from the sleeve with an adjustable length, and the finger support is coupled with the shaft.

The first support comprises an auxiliary fixer and at least one cushion, and the auxiliary fixer is provided at a free end of the first support.

The first support has a fixing hole and the at least one cushion has an adjustment groove. A screwing member is provided in the adjustment groove and is detachably screwed into the fixing hole.

The first support has an adjustment groove. The fixing hole is located in the adjustment groove of the first support. A positioning member is provided in the adjustment groove of the at least one cushion. The positioning member is slidably coupled with the adjustment groove of the first support.

Furthermore, the invention discloses a signal generator of a motor coordination testing device including a first electronic protractor and a first support rotatably coupled with the first electronic protractor.

The signal generator of the motor coordination testing device further comprises a second electronic protractor and a second support rotatably coupled with the second electronic protractor, with the second electronic protractor coupled with the first support.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 6a shows a displayed result of the signal retrieving device of the first embodiment of the invention.

FIG. 6b shows another displayed result of the signal retrieving device of the first embodiment of the invention.

FIG. 7 shows an analysis diagram of the motor coordination testing device of the first embodiment of the invention.

Figure 1:
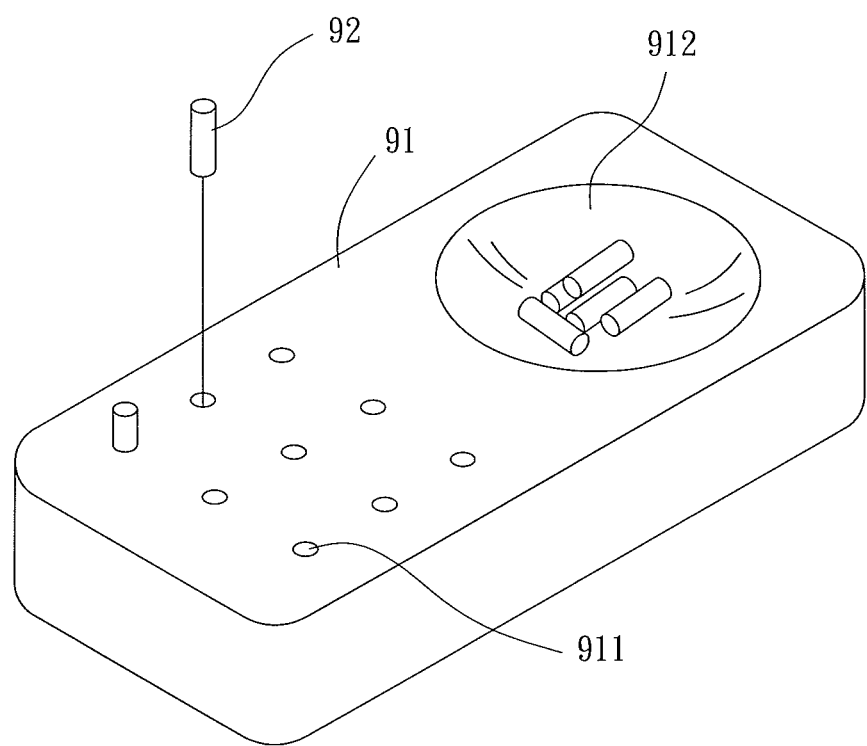
FIG. 1 shows a conventional motor coordination testing device.

In the various figures of the drawings, the same numerals designate the same or similar parts. Furthermore, when the terms "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Figure 2:
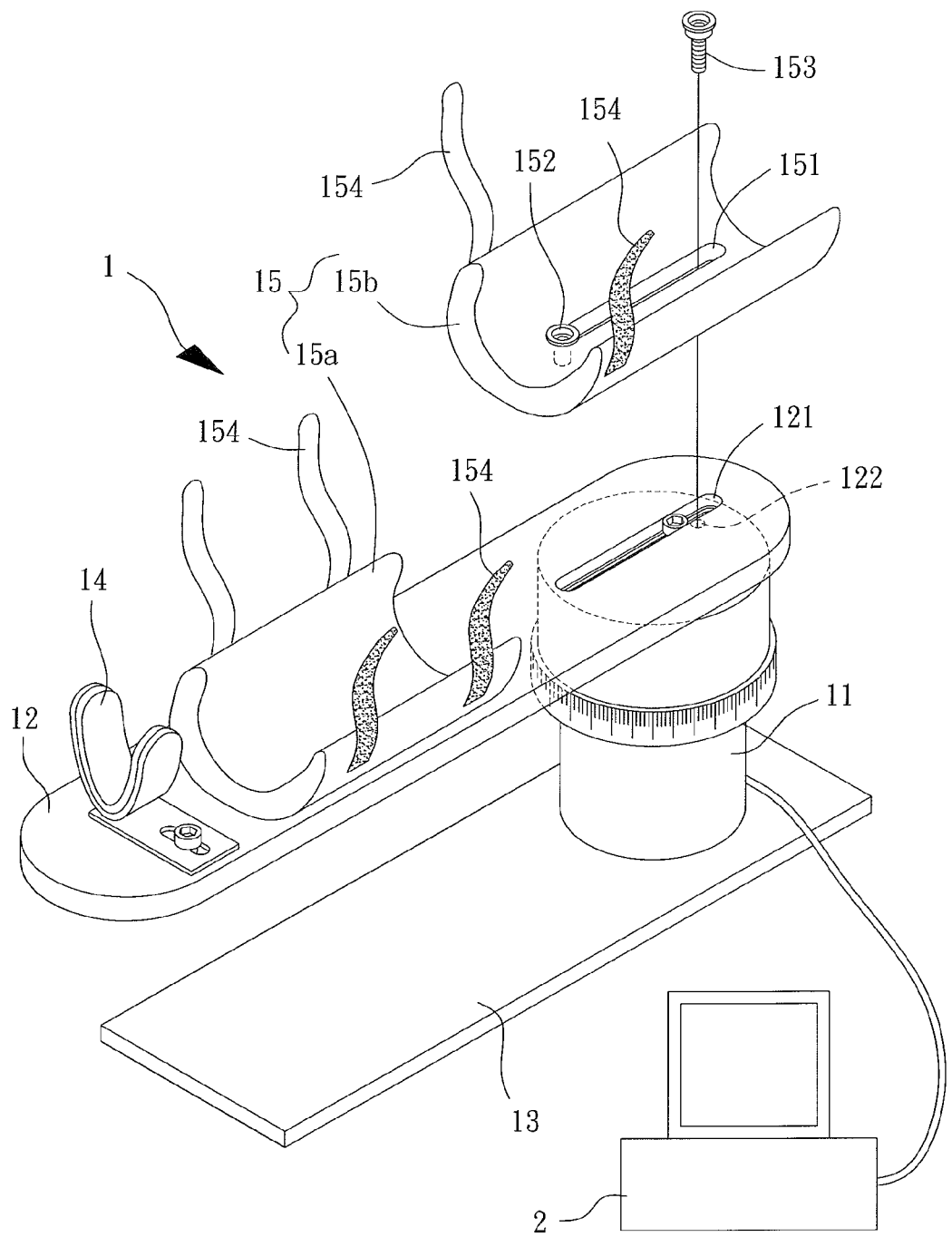
FIG. 2 is an exploded view of a motor coordination testing device according to a first embodiment of the invention.

Referring to FIG. 2, an exploded view of a motor coordination testing device is disclosed according to a first embodiment of the invention. The motor coordination testing device includes a signal generator 1 and a signal retrieving device 2 electrically connected to the signal generator 1. A testee may put his/her limb on the signal generator 1 and moves his/her limb on the signal generator 1 for testing. The turning angle obtained from limb movement is then converted into electronic signals to be retrieved by the signal retrieving device 2.

The motor coordination testing device of the first embodiment has a single turning mechanism and is directed to testing the motor coordination of an elbow joint of the testee. However, the structure of the signal generator 1 can be modified in any form fitted to other limb joints to be tested, as can be appreciated by one skilled in the art.

In the embodiment, the signal generator 1 includes a first electronic protractor 11 and a first support 12. The first electronic protractor 11 is electrically connected to the signal retrieving device 2. The first support 12 is coupled with the first electronic protractor 11 and capable of turning on the first electronic protractor 11 at a center of the first electronic protractor 11. Preferably, the first support 12 is coupled with the top face of the first electronic protractor 11. The testee can put his/her forearm on the first support 12 and turns the first support 12 with the forearm. When the testee is turning the first support 12 with his forearm, the first electronic protractor 11 may detect the turning angle of the first electronic protractor 11 and produces an electronic signal. The first electronic protractor 11 is arranged in a manner that permits the first support 12 to turn relative to the first electronic protractor 11 almost without friction, allowing the testee to hardly apply any muscle strength to turn the first support 12. Thus, even a testee with muscle weakness can operate the motor coordination testing device of the invention to test his/her motor coordination.

Furthermore, the first electronic protractor 11 may have a proper height and is mounted on a base 13, allowing the signal generator 1 to be stably placed on a desk. Thus, the testee can easily put his/her forearm on the first support 12 for testing.

Moreover, an auxiliary fixer 14 and at least one cushion 15 may be provided on the first support 12. The auxiliary fixer 14 is provided around a free end of the first support 12 for supporting the hand of the testee. The at least one cushion 15 is provided to support the forearm of the testee.

In the embodiment, the at least one cushion 15 may consist of two cushions 15 respectively numbered as 15a and 15b. The cushion 15b where the testee puts his/her forearm may align with the first support 12 to allow patients with different forearm lengths to use the motor coordination testing device. The first support 12 may have an adjustment groove 121 and a fixing hole 122 located in the adjustment groove 121. The cushion 15b also has an adjustment groove 151 aligned with the adjustment groove 121 of the first support 12. A positioning member 152 and a screwing member 153 may be provided in the adjustment groove 151. The positioning member 152 can slide in the adjustment groove 121 of the first support 12. The screwing member 153 may screw into the fixing hole 122 when the cushion 15b is adjusted to a proper position.

The at least one cushion 15 may be in a concave, arcuate form to stably support and receive the forearm of the testee, providing the testee with greater comfort during testing. The at least one cushion 15 may further include at least one cohering, fastening member 154 to wind around the forearm of the testee, avoiding the forearm of the testee from sliding out of the first support 12 during testing. Thus, arrangement of the auxiliary fixer 14 and/or the at least one cohering, fastening member 154 allows the forearm of the testee to be fixed on the first support 12 more stably. In another aspect, the auxiliary fixer 14 that supports the hand of the testee may allow the testee to put his/her forearm on the first support 12 without keeping his/her hand straight, improving the operability of the motor coordination testing device. Therefore, even a testee with muscle weakness can operate the proposed device.

Figure 3:
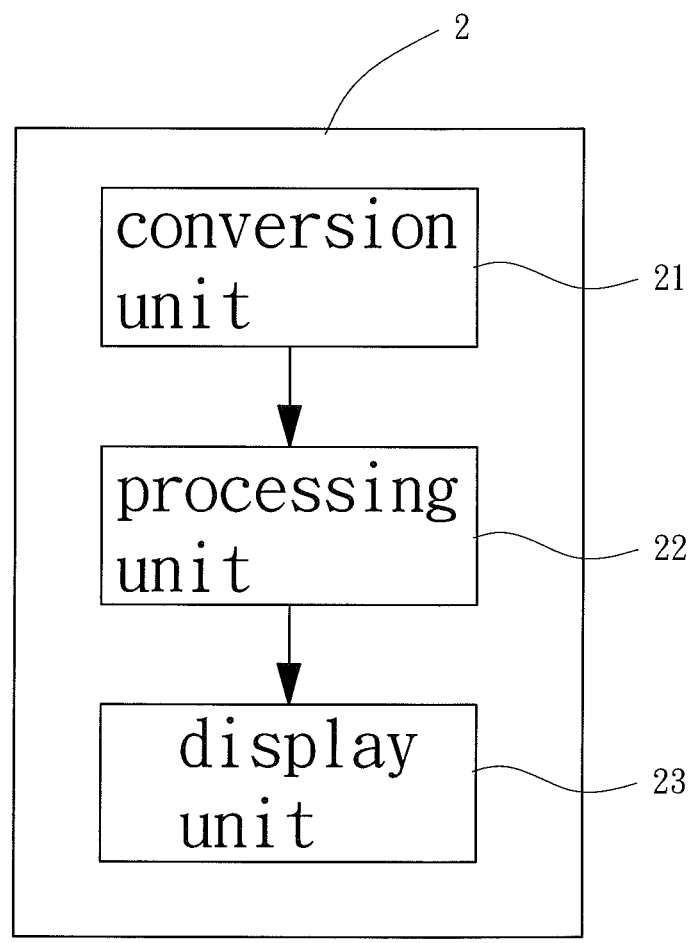
FIG. 3 shows a systematic diagram of a signal retrieving device of the motor coordination testing device of the first embodiment of the invention.

Referring to FIGS. 2 and 3, the signal retrieving device 2 retrieves the electronic signals generated during turning of the first electronic protractor 11. In this embodiment, the signal retrieving device 2 comprises a conversion unit 21, a processing unit 22 and a display unit 23. The conversion unit 21 may be a conventional A/D converter that converts the analog signals generated during turning of the first electronic protractor 11 into digital signals readable for the processing unit 22. After the digital signals are processed by the processing unit 22, the display unit 23 may display a mark on a corresponding location.

Figure 4:
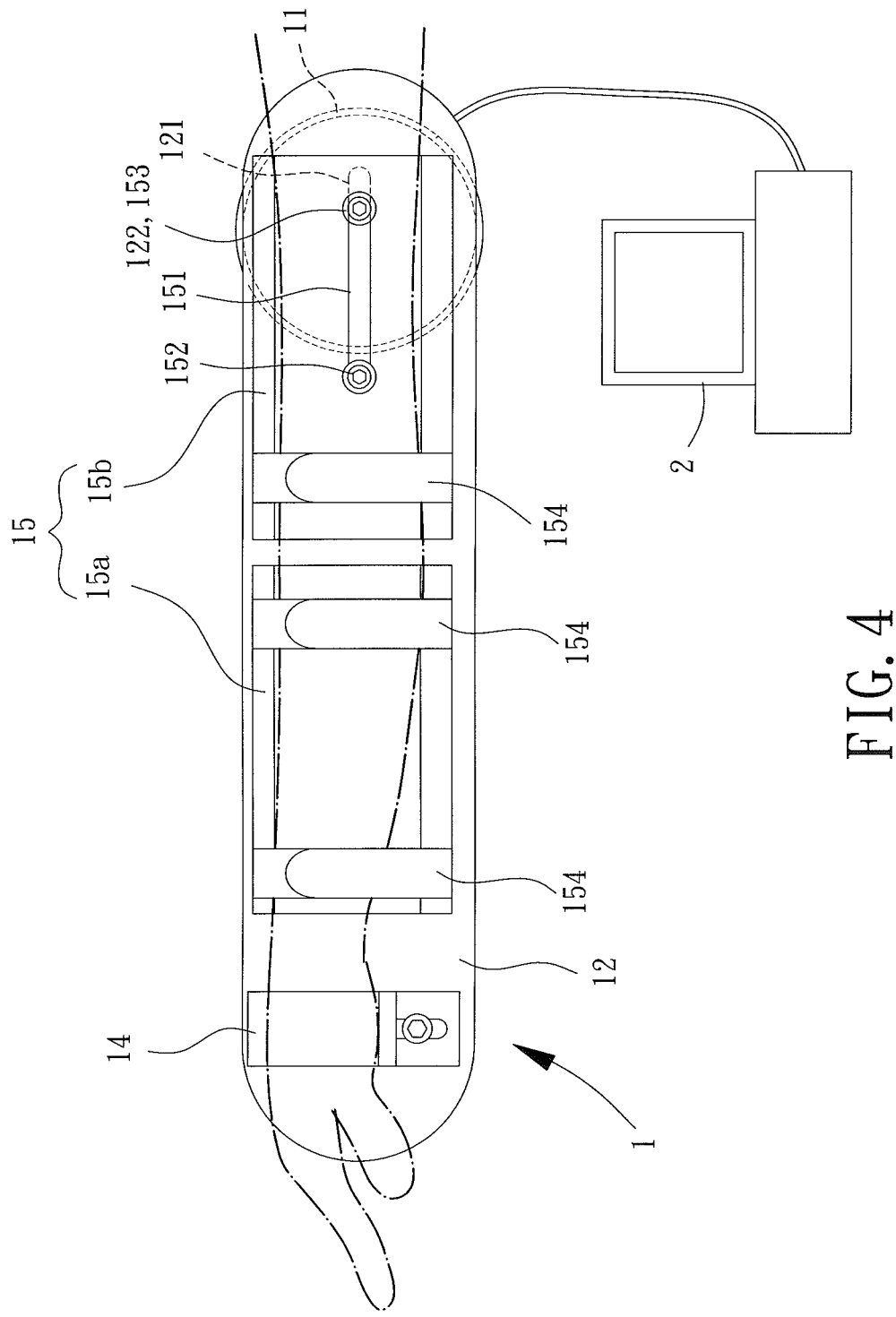
FIG. 4 is a top cross-sectional view of the motor coordination testing device of the first embodiment of the invention.

Referring to FIGS. 4 and 6a, when the test is about to start, the testee can put his/her forearm on the first support 12 and stretch his/her hand into the auxiliary fixer 14 (if installed), allowing his/her forearm to be supported by the cushions 15a and 15b. After the testee properly locates his/her forearm on the first support 12, the at least one cohering, fastening member 154 is wound around the forearm of the testee for fixing purposes. At this time, the display unit 23 displays a target cursor T and a tracking cursor Tt on a predetermined location. In FIG. 6a, the target cursor T is shown as a rectangular frame, and the tracking cursor Tt is shown as a cross. The target cursor T may show a to-be-traced target generated by a test program of the device. The tracking cursor Tt may show information regarding speed and turning angle generated by the testee turning the first support 12 with his/her forearm. Initially, the target cursor T and the tracking cursor Tt are overlapped.

Figure 5:
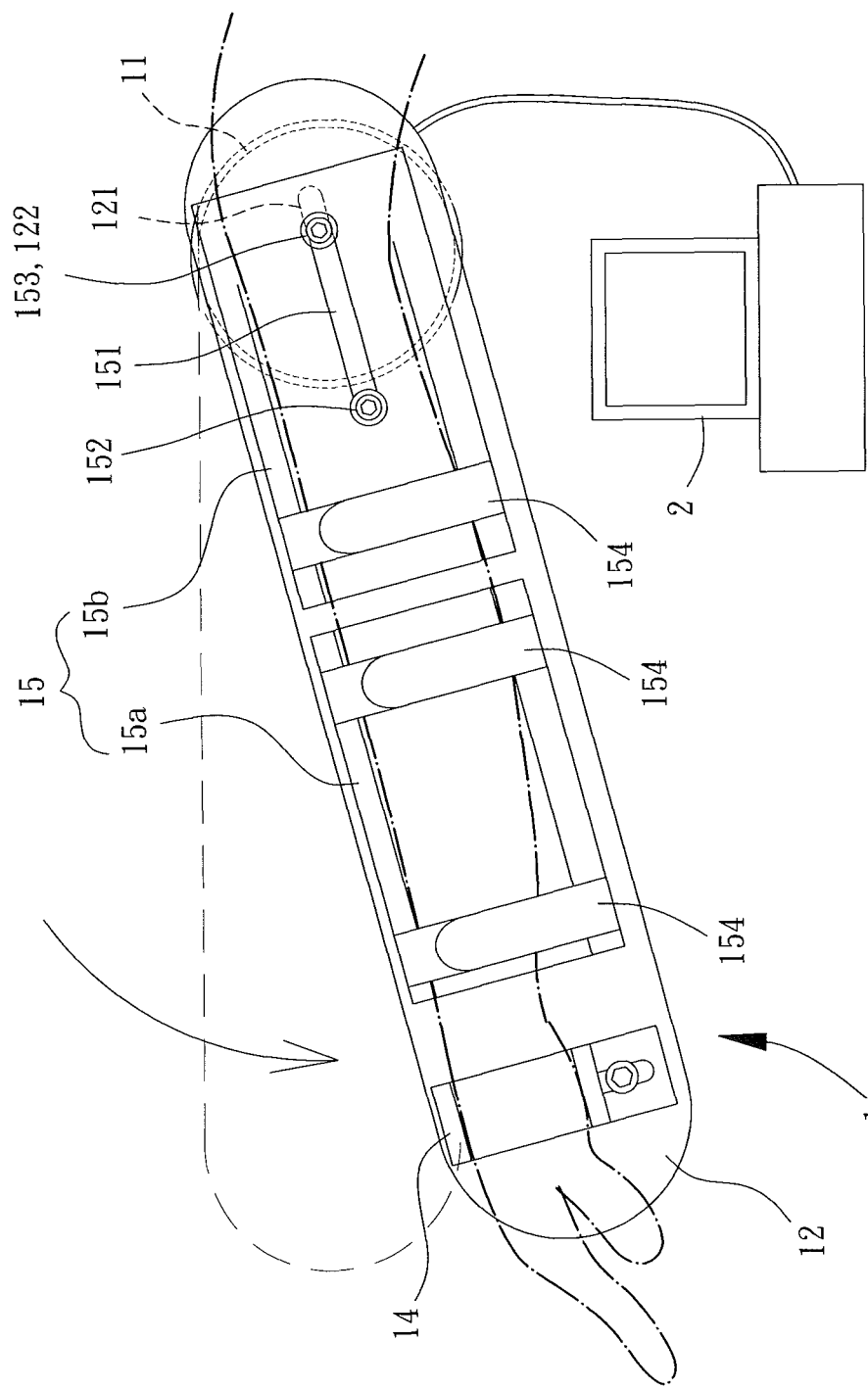
FIG. 5 shows an operation diagram of the motor coordination testing device of the first embodiment of the invention.

Referring to FIGS. 5 and 6b, the target cursor T moves continuously in a random speed during testing. At this point, the testee is required to turn his/her forearm in an attempt to trace the target cursor T with the tracking cursor Tt. In this manner, the motor coordination of the testee can be determined.

In this mechanism, the motor coordination testing device of the invention can record the needed information in the whole course, and outputs an analysis diagram as shown in FIG. 7. In FIG. 7, the solid line represents the movement track of the target cursor T, and the dotted line represents the movement track of the tracking cursor Tt. Through the information quantification, it can be determined which motions the testee can smoothly perform without any difficulty and which motions the testee has a hard time performing, allowing the diagnostician to provide a correct and objective analysis as to the motor coordination of the testee. Hence, not only can the motor coordination testing device determine whether the physical disability of the testee is caused by muscle weakness or poor physical coordination (in which case the testee will be given a correct recommendation as to how to proceed in rehabilitation), but it can also serve as a rehabilitation device on which the testee can work to regain his/her physical ability through constant exercise.

Figure 8:
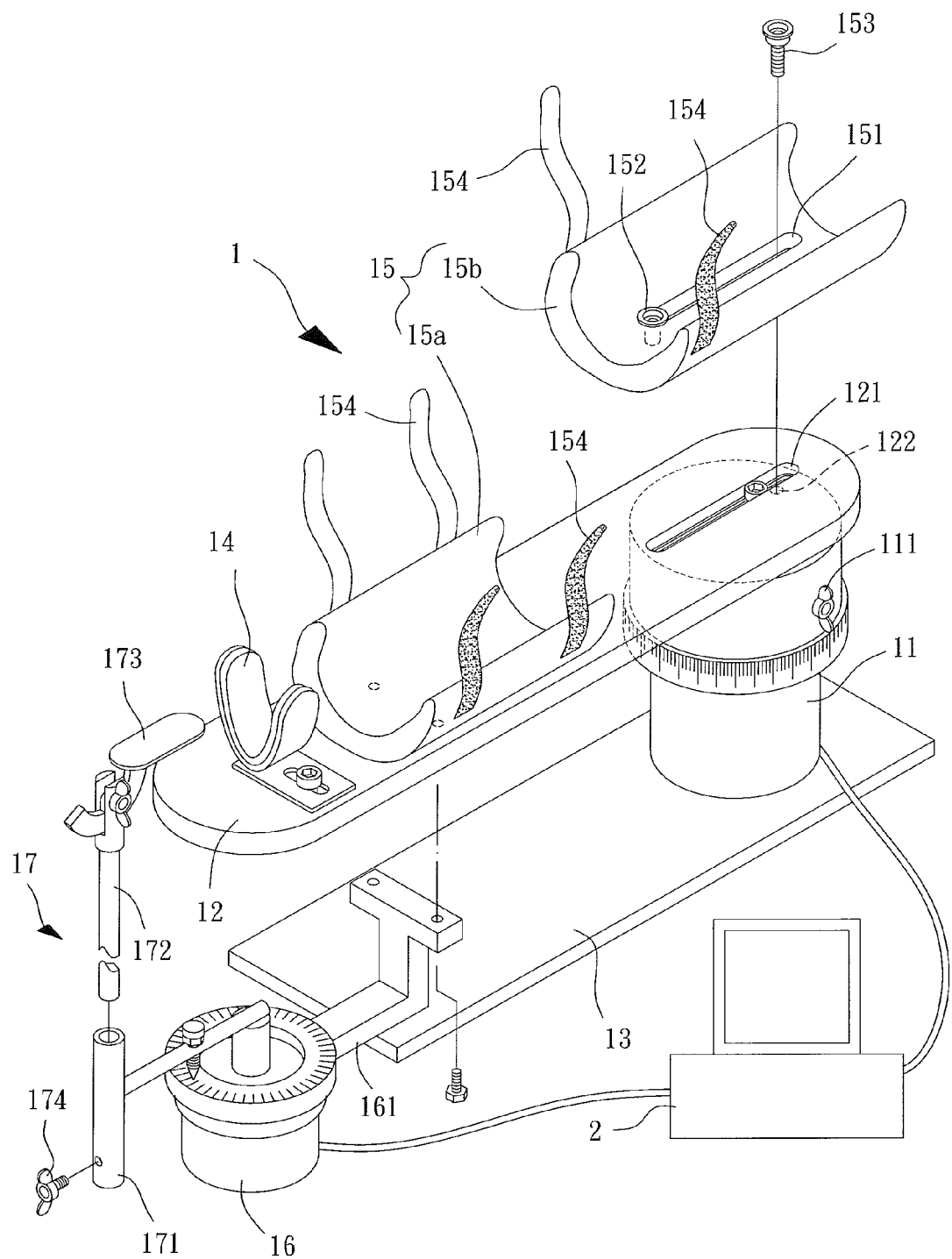
FIG. 8 is an exploded view of a motor coordination testing device according to a second embodiment of the invention.

Referring to FIG. 8, an exploded view of a motor coordination testing device is shown according to a second embodiment of the invention. In the second embodiment, the motor coordination testing device provides double turning mechanisms and is directed to testing the motor coordination of an elbow joint and a finger joint.

The second embodiment differs from the first embodiment in that the signal generator 1 further comprises a second electronic protractor 16 and a second support 17. The second support 17 is coupled with the second electronic protractor 16 and capable of turning on the second electronic protractor 16 at a center of the second electronic protractor 16. The second electronic protractor 16 is electrically connected to the first electronic protractor 11 and the signal retrieving device 2.

In this embodiment, a connection member 161 may be provided on an outer circumferential wall of the second electronic protractor 16. The connection member 161 is screwed to a bottom face of the first support 12, allowing the second electronic protractor 16 and the first support 12 to turn relatively to the first electronic protractor 11 at the same time. In the embodiment, the first electronic protractor 11 may further comprise a turning control member 111. The turning control member 111 can be turned to control whether the first support 12 can turn relative to the first electronic protractor 11.

The second support 17 may comprise a sleeve 171, a shaft 172 and a finger support 173. The shaft 172 is extended into the sleeve 171. An adjustment member 174 may be provided on the sleeve 171 to adjust the length of the shaft 172 protruding from the sleeve 171, to allow the testee to easily put his/her finger on the finger support 173 based on his/her finger position. In this embodiment, the sleeve 171 is connected to the second electronic protractor 16, and the finger support 173 is coupled on the shaft 172. However, the sleeve 171 and the shaft 172 may also be connected in an opposite manner. Namely, the shaft 172 is connected to the second electronic protractor 16 and the finger support 173 is connected to the sleeve 171, as can be readily appreciated by one skilled in the art.

In such an arrangement, the motor coordination testing device of the second embodiment can test the motor coordination for two kinds of limb joints. When the motor coordination of the elbow joint is under test, the turning control member 111 of the first electronic protractor 11 is unlocked, allowing the first support 12 to turn relative to the first electronic protractor 11.

Figure 9:
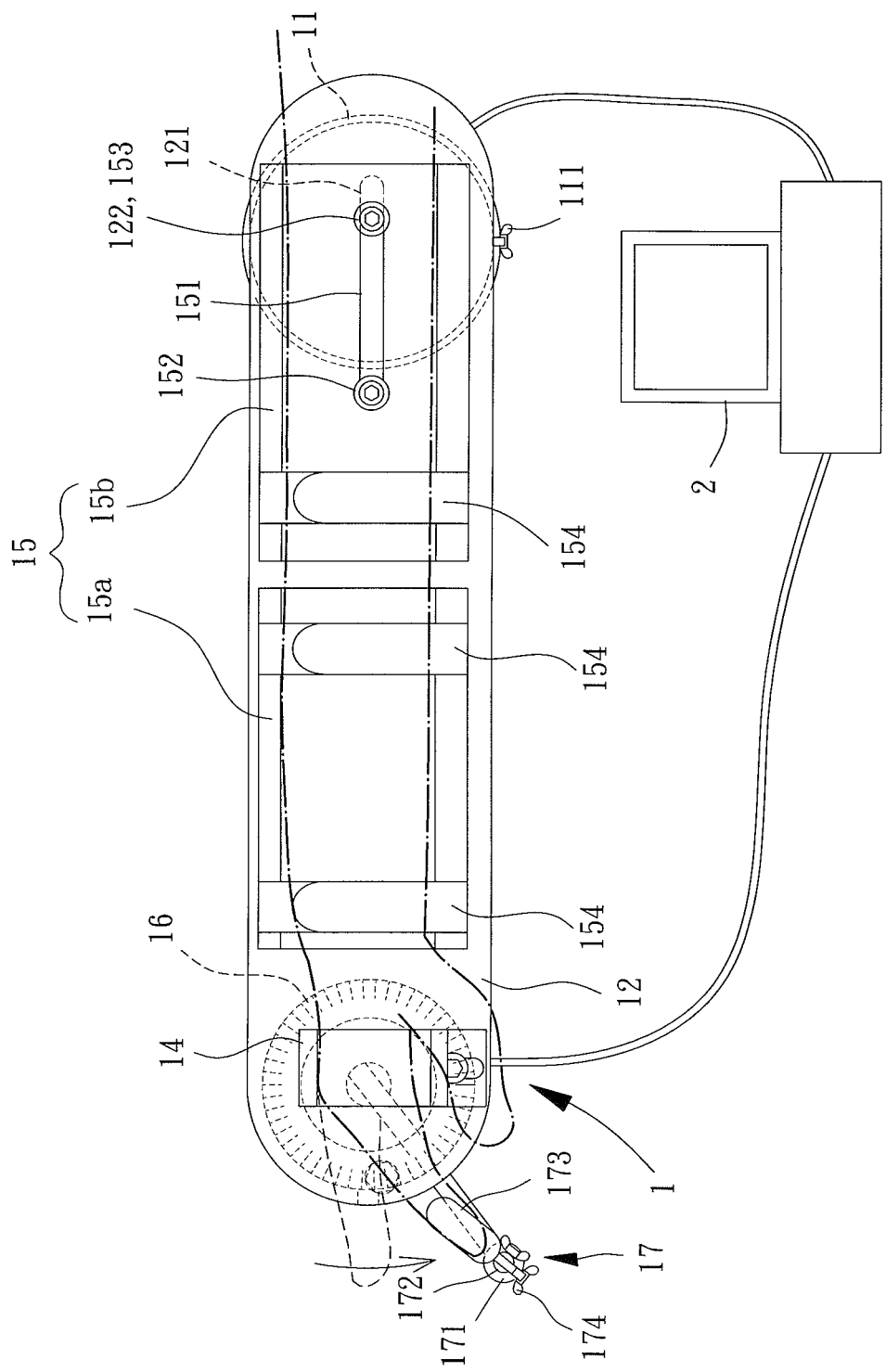
FIG. 9 is a top cross-sectional view of the motor coordination testing device of the second embodiment of the invention, in which the motor coordination of a finger joint of a testee is tested.

Referring to FIGS. 9 and 6b, when the motor coordination of the finger joint is under test, the turning control member 111 of the first electronic protractor 11 is locked, prohibiting the first support 12 from turning relative to the first electronic protractor 11.

Therefore, the testee can put his/her hand on the auxiliary fixer 14 to keep his/her hand straight and moves his/her finger to turn the second support 17 relative to the second electronic protractor 16. Thus, through electrical connection between the second electronic protractor 16 and the signal retrieving device 2, information regarding speed and turning angle generated by the finger movement of the testee can be displayed on the display unit 23 in terms of the tracking cursor Tt.

In summary, the motor coordination testing device of the invention can record all the information needed in the whole course by data quantification, allowing a diagnostician to provide a correct analysis by analyzing the testing result of the proposed device. Therefore, the testee can be given a correct recommendation as to rehabilitation.

The motor coordination testing device of the invention can test the motor coordination of a testee without requiring the testee to apply much muscle force. Therefore, even the patient with muscle weakness is allowed to use the motor coordination testing device to test his/her motor coordination. As such, the motor coordination testing device of the invention can provide accurate analysis and diagnosis towards motor coordination of the testee.

The signal generator of the motor coordination testing device of the invention can generate electronic signals according to turning of the limb of the testee, to provide quantified data for analysis. Through the analysis diagram of the testing result, the motor coordination of the testee towards individual motions can be determined. Thus, the testee can choose the most appropriate rehabilitation manner to regain his/her physical ability.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A signal generator of a motor coordination testing device comprising:
   a first electronic protractor;
   a first support rotatably coupled with the first electronic protractor;
   a second electronic protractor, wherein the first and second electronic protractors have rotation axes parallel to and spaced from each other; and
   a second support rotatable coupled with the second electronic protractor, wherein the second electronic protractor is coupled with the first support, wherein the second support comprises a sleeve, a shaft and a finger support, wherein the sleeve is connected to the second electronic protractor, wherein the shaft is extended into the sleeve and protrudes from the sleeve with an adjustable length, wherein the finger support is coupled with the shaft, and wherein the sleeve and the shaft are parallel to the rotation axes of the first and second electronic protractors.

2. The signal generator of the motor coordination testing device as claimed in claim 1, wherein the second electronic protractor comprises a connection member fixed to the first support, and wherein the first electronic protractor comprises a turning control member controlling whether the first support turns relative to the first electronic protractor.

3. The signal generator of the motor coordination testing device as claimed in claim 1, wherein the first support comprises an auxiliary fixer and at least one cushion, and the auxiliary fixer is provided at a free end of the first support.

4. The signal generator of the motor coordination testing device as claimed in claim 3, wherein the first support has a fixing hole, the at least one cushion has an adjustment groove, a screwing member is provided in the adjustment groove, and the screwing member is detachably screwed into the fixing hole.

5. The signal generator of the motor coordination testing device as claimed in claim 4, wherein the first support has an adjustment groove, the fixing hole is located in the adjustment groove of the first support, a positioning member is provided in the adjustment groove of the at least one cushion, and the positioning member is slidably coupled with the adjustment groove of the first support.

6. A motor coordination testing device comprising:
   a signal generator comprising a first electronic protractor, a second electronic protractor, a first support rotatably coupled with the first electronic protractor, and a second support rotatably coupled with the second electronic protractor, wherein the first and second electronic protractors have rotation axes parallel to and spaced from each other, wherein the second support comprises a sleeve, a shaft and a finger support, wherein the sleeve is connected to the second electronic protractor, wherein the shaft is extended into the sleeve and protrudes from the sleeve with an adjustable length, wherein the finger support is coupled with the shaft, and wherein the sleeve and the shaft are parallel to the rotation axes of the first and second electronic protractors; and
   a signal retrieving device electrically connected to the signal generator, wherein the second electronic protractor is coupled with the first support and electrically connected to the signal retrieving device.

7. The motor coordination testing device as claimed in claim 6, wherein the signal retrieving device comprises a conversion unit, a processing unit and a display unit, the conversion unit is electrically connected to the first electronic protractor and the processing unit, and the processing unit is electrically connected to the display unit.

8. The motor coordination testing device as claimed in claim 6, wherein the signal retrieving device comprises a conversion unit, a processing unit and a display unit, the conversion unit is electrically connected to the first and second electronic protractors and the processing unit, and the processing unit is electrically connected to the display unit.

9. The motor coordination testing device as claimed in claim 6, wherein the second electronic protractor comprises a connection member fixed to the first support, and wherein the first electronic protractor comprises a turning control member controlling whether the first support turns relative to the first electronic protractor.

10. The motor coordination testing device as claimed in claim 6, wherein the first support comprises an auxiliary fixer and at least one cushion, and the auxiliary fixer is provided at a free end of the first support.

11. The motor coordination testing device as claimed in claim 10, wherein the first support has a fixing hole, the at least one cushion has an adjustment groove, a screwing member is provided in the adjustment groove, and the screwing member is detachably screwed into the fixing hole.

12. The motor coordination testing device as claimed in claim 8, wherein the first support has an adjustment groove, the fixing hole is located in the adjustment groove of the first support, a positioning member is provided in the adjustment groove of the at least one cushion, and the positioning member is slidably coupled with the adjustment groove of the first support.

* * * * *